United States Patent
Zeldis et al.

(10) Patent No.: US 7,435,726 B2
(45) Date of Patent: Oct. 14, 2008

(54) COMPOSITIONS AND METHODS FOR THE TREATMENT OF CANCER

(75) Inventors: Jerome B. Zeldis, Princeton, NJ (US); Andrew L. Zeitlin, Basking Ridge, NJ (US); Sol Barer, Westfield, NJ (US)

(73) Assignee: Celgene Corporation, Summit, NJ (US)

( * ) Notice: Subject to any disclaimer, the term of this patent is extended or adjusted under 35 U.S.C. 154(b) by 117 days.

(21) Appl. No.: 09/853,617

(22) Filed: May 14, 2001

(65) Prior Publication Data

US 2002/0035090 A1   Mar. 21, 2002

(51) Int. Cl.
- *A01N 43/00* (2006.01)
- *A61K 31/33* (2006.01)
- *A01N 43/04* (2006.01)
- *A61K 31/70* (2006.01)

(52) U.S. Cl. .......................... 514/183; 514/23; 514/25; 544/60; 544/125; 544/361; 546/48

(58) Field of Classification Search ............. 514/23, 514/25, 183; 544/60, 125, 361; 546/48
See application file for complete search history.

(56) References Cited

U.S. PATENT DOCUMENTS

| | | | |
|---|---|---|---|
| 4,604,463 A | 8/1986 | Miyasaka et al. | 544/125 |
| 5,385,901 A | 1/1995 | Kaplan et al. | 514/231.5 |
| 5,593,990 A | 1/1997 | D'Amato | 514/235.2 |
| 5,622,959 A * | 4/1997 | Priel et al. | 514/283 |
| 5,629,327 A | 5/1997 | D'Amato | 514/323 |
| 5,643,915 A | 7/1997 | Andrulis, Jr. et al. | 514/279 |
| 5,654,312 A | 8/1997 | Andrulis, Jr. et al. | 514/279 |
| 5,712,291 A | 1/1998 | D'Amato | 514/323 |

FOREIGN PATENT DOCUMENTS

WO   WO 94/20085   9/1994

OTHER PUBLICATIONS

Marx et al. Proc. Am. Soc. Clin. Onocology (1999), vol. 18, p. 454a.*
Pitot et al. Journal of Clinical Onocology (1997), vol. 15, pp. 2910-2919.*
Hecht, Jr. Oncology (1998), 12(8 Suppl. 6): 72-8 (Abstract).*
Houghton et al. Cancer Chemother Pharmacol (1995), vol. 36, pp. 393-403.*
Avgeropoulos et al., *The Oncologist* 4:209-224 (1999).
Bach et al., *Acta Pathol. Microbiol. Scand.* 59:491-499 (1963).
Bach et al., *The Lancet* 71:1271 (1963).
Braun et al., *Biochem. Biophys. Res. Comm.* 98(4):1029-1034 (1981).
Chaundry et al., *Cancer Res.* 26:1884-1886 (1966).
Costa et al., *Blood* 92 (10:suppl. 1):235b (1998).
Cunningham et al., *The Lancet* 352(9138):1413-1418 (1998).
D'Amato et al., *Proc. Natl. Acad. Sci.* 91:4082-4085 (1994).
De et al., *J. Pharm. Sci.* 64(2):262-266 (1975).
DiPaolo et al., *Proc. Soc. Exp. Biol. And Med.* 114:384-387 (1963).
DiPaolo et al., *Science* Jun. 26, 1964:1583 (1964).
DiPaolo et al., *Cancer Chemo. Reports* 29:99-102 (1963).
Ehrenpreis et al., *Gastroenterology* 117:1271-1277 (1999).
Gershbein, *Riv. Pathol. Nerv. Ment.* 87(4):88-92 (1966).
Grabstald et al., *Clin. Pharmacol. And Ther.* 6(3):298-302 (1965).
Hatfill et al., *Leuk. Res.* 15(2-3):129-136 (1991).
Koch, *Prog. Med. Chem.* 22:165-242 (1985).
Lenicque, *Acta Zool.* 48:128-139 (1967).
Marx et al., *Proc. Am. Soc. Clin. Oncology* 18:454a (1999).
McCann, *Drug Topics* 41-42 (Jun. 21, 1999).
McHugh et al., *Clin. Exper. Immunol.*, 99:160-167 (1995).
Miura et al., *Experientia* 26:305-306 (1970).
Mohri et al., *Chem. Pharm. Bull.* 16:2289-2292 (1968).
Moller et al., *J. Immunol.* 159:5157-5161 (1997).
Moreira et al., *J. Expr. Med.* 177:1675-1680 (1993).
Muckter, *Antimicrobial Agents and Chemotherapy* 531-538 (1965).
Mummery et al., *Toxicol. Lett.* 18(3):201-209 (1983).
Olson et al., *Clin. Pharmacol. And Ther.* 6:293-297 (1965).
Physician's Desk Reference, 2412-2418 (54th ed., 2000).
Physician's Desk Reference, 911-916 (54th ed., 2000).
Pitot et al., *J. Clin. Oncology* 15(8):2910-2919 (1997).
Robbins et al., *Basic Pathology*, 2nd ed., W.B. Saunsers Co., Philadelphia, pp. 68-79 (1976).
Roe et al., *Nature* 200:1016-1017 (1963).
Rothenberg, *Annals of Oncology* 8:837-855 (1997).
Rothenberg et al., *Cancer* 85(4):786-795 (1999).
Rothenberg et al., *J. Clin. Oncology* 14(4):1128-1135 (1996).
Singhal et al., *New England J. Med.* 341(21):1565-1571 (1999).
Sugiura et al., *GANN* 55:57-60 (1964).
Vasiliauskas et al., *Gastroenterology* 117:1278-1287 (1999).
Villa et al., *Haematol. Latina* 6:217-221 (1963).
Villa et al., *The Lancet*, Mar. 30, 1963, 725 (1963).
Woodyatt, *The Lancet*, Apr. 7, 1962, 750 (1962).
Zwart, *Arzneim-Forsch.* 16(12):1688-1689 (1966).
R. Govindarajan et al., *Lancet (North American Edition)*, 2000, vol. 356, No. 9229, pp. 566-567.
Cao et al. *British Journal of Cancer* 80:716-723 (1999).
Burton et al., *Current Opinion in Oncology*, 11(3): 157-161 (1999).
Cheston et al., *Seminars in Oncology*, 27(5): 560-577 (2000).
Mundle et al., *Blood*, 96(11): 146a (2000).
*Bioworld Today*, Nov. 4, 2005, p. 2.
Hecht, J.R., "Gastrointestinal Toxicity of Irinotecan," *Oncology*, 12(8 Suppl. 6): 72-8 (1998).

* cited by examiner

*Primary Examiner*—Patrick T Lewis
(74) *Attorney, Agent, or Firm*—Jones Day

(57) ABSTRACT

This invention relates to compositions comprising thalidomide and another anti-cancer drug which can be used in the treatment or prevention of cancer. Preferred anti-cancer drugs are topoisomerase inhibitors. A particular composition comprises thalidomide, or a pharmaceutically acceptable salt, solvate, or clathrate thereof, and irinotecan. The invention also relates to methods of treating or preventing cancer which comprise the administration of a thalidomide and another anti-cancer drug to a patient in need of such treatment or prevention. The invention further relates to methods of reducing or avoiding adverse side effects associated with the administration of chemotherapy or radiation therapy which comprise the administration of thalidomide to a patient in need of such reduction or avoidance.

10 Claims, No Drawings

COMPOSITIONS AND METHODS FOR THE TREATMENT OF CANCER

1. FIELD OF THE INVENTION

This invention relates to pharmaceutical compositions comprising thalidomide and an anti-cancer agent, particularly a topoisomerase inhibitor, to methods of treating cancer, and to methods of reducing or avoiding adverse effects associated with anti-cancer agents such as topoisomerase inhibitors.

2. BACKGROUND OF THE INVENTION

The incidence of cancer continues to climb as the general population ages, as new cancers develop, and as susceptible populations (e.g., people infected with AIDS) grow. A tremendous demand therefore exists for new methods and compositions that can be used to treat patients with cancer.

2.1. PATHOBIOLOGY OF CANCER

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor preneoplastic changes, which may under certain conditions progress to neoplasia.

Pre-malignant abnormal cell growth is exemplified by hyperplasia, metaplasia, or most particularly, dysplasia (for review of such abnormal growth conditions, see Robbins and Angell, 1976, *Basic Pathology*, 2d Ed., W. B. Saunders Co., Philadelphia, pp. 68-79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., *Immunology*, 17.1-17.12 (3rd ed., Mosby, St. Louis: 1993).

Descriptions of only a few types of cancers are provided below. Characteristics of other types of cancers are well known to medical practitioners, and are described in the medical literature.

2.2. AIDS-RELATED NON-HODGKIN'S LYMPHOMA

AIDS has been closely associated with a variety of cancers. Further, the types of malignancies and their incidence rates are increasing as the development of effective antiretroviral therapies and prophylaxis against opportunistic infections leads to prolonged survival in the immunodeficient state for AIDS patients. Karp and Broder, *Cancer Res.* 51:4747-4756 (1991). AIDS-related non-Hodgkin's lymphoma is a very aggressive disease with a very high incidence of central nervous system involvement. Since its discovery in 1981, the incidence of AIDS-related non-Hodgkin's lymphoma has reportedly increased. One reason for such an observation is that patients infected with the AIDS virus now live longer than they used to.

2.3. PRIMARY AND METASTATIC CNS TUMORS

The incidence of primary and metastatic brain tumors is also increasing in the United States. Unfortunately, the arsenal of chemotherapeutics for these types of cancers is minimal, while the need for such therapeutics is high.

Glioblastoma multiform and other primary and metastatic central nervous system tumors are devastating malignancies. The treatment of these tumors include surgery, radiation therapy and treatment with agents such as the nitrosourea BCNU. Other chemotherapeutic agents utilized include procarbazine, vincristine, hydroxyurea and cisplatin. But even when all three modalities (surgery, radiation therapy and chemotherapy) are utilized, the average survival of patients with central nervous system malignancies is only about 57 weeks. Clearly, new treatment approaches are needed both for patients with newly diagnosed primary and metastatic central nervous system tumors, as well as for patients with such tumors which are refractory to the above modalities.

2.4. BREAST, LUNG, BLADDER AND PROSTATE CANCERS

In the United States, the cumulative risk of developing breast cancer is reportedly about 10.2 percent. *The Merck Manual* 1815 ($16_{th}$ ed. 1992). The treatment for early breast cancer is surgery, with or without radiation therapy, or surgery, with or without radiation therapy, plus chemotherapy and/or hormonal therapy. Current chemotherapy for patients with primary or metastatic breast cancer includes treatment with cyclophosphamide, methotrexate, doxorubicin, 5-fluorouracil, cisplatin, vinblastine, taxol, taxotere, mitomycin C and occasionally other agents. Unfortunately, even with these agents, almost all women who develop metastatic breast cancer succumb to their disease. One particular place that metastatic breast cancer does metastasize to is the central nervous system. When central nervous system metastases do occur, the usual treatment is surgery (for a solitary metastasis) or radiation, or surgery plus radiation therapy.

Lung cancer is reportedly the leading cause of cancer death in men and women. *The Merck Manual* 731 ($16^{th}$ ed. 1992). A variety of causes exist, but cigarette smoking accounts for greater than 90 percent of reported cases in men and greater than 70 percent of reported cases in women. Id.

Most patients with lung cancer present a tumor that has already metastasized to a variety of organs, including lung, liver, adrenal gland and other organs. Treatment of metastatic lung cancer is not yet standardized. Ihde, D.C., *The New England Journal of Medicine* 327:1434-1441 (1992). However, chemotherapy regimens that are utilized include treatment with cisplatin plus etoposide, combinations of cyclophosphamide plus doxorubicin plus cisplatin, and single agents alone or in combination, including ifosfamide, teniposide, vindesine, carboplatin, vincristine, taxol, nitrogen mustard, methotrexate, hexamethylmelamine and others. Despite these chemotherapeutic regimens the average patient with metastatic lung cancer still only survives 7-12 months. One particular troublesome place for metastases of lung cancer is the central nervous system. The treatment for central nervous system metastases includes surgery (to remove a solitary lesion), radiation therapy, or a combination of both.

Each year about 50,000 new cases of bladder cancer are reported in the United States. *The Merck Manual* 1749 (16$^{th}$ ed. 1992). Although at presentation the disease is usually localized, most patients develop distant metastatic disease. The most recent advances have been in the area of chemotherapy for patients with such metastatic disease. One effective regimen is called the MVAC regimen. It consists of treatment with methotrexate plus vinblastine plus adriamycin (doxorubicin) plus cisplatin. Although the response rate is high to this chemotherapeutic regimen, medical oncologists are noting that one place the patients fail is with metastases to the central nervous system.

It is estimated that more than 120,000 men will be diagnosed with prostate cancer this year. *The Merck Manual* 1750 (16$^{th}$ ed. 1992). The most common sites of metastases in patients with prostate cancer are the bone and lymph nodes. The bone metastases are particularly bothersome in that they can create intense pain for the patient. The current treatment for metastatic prostate cancer includes treatment with flutamide, leuprolide, diethylstilbestrol, and other hormonal manipulations, as well as chemotherapy (doxorubicin, estramustine phosphate, vinblastine, suramin, cisplatin, and others). Unfortunately, none of these agents are consistently helpful in the disease. In addition, as patients with prostate cancer live longer with their malignancy, they will most likely develop a higher incidence of metastases to the central nervous system (including the spinal cord).

2.5. ESOPHAGEAL CANCER

Several years ago, carcinoma of the esophagus reportedly represented only about six percent of all cancers of the gastrointestinal tract; however, it reportedly caused a disproportionate number of cancer deaths. Boring, C. C., et al., *CA Cancer J. Clin.* 43:7 (1993). These cancers usually arise from the epithelial layer of the esophagus and are either squamous cell carcinomas or adenocarcinomas. Overall, the 5 year survival is about five percent.

2.6. LEUKEMIA

Leukemia refers to malignant neoplasms of the bloodforming tissues. Although viruses reportedly cause several forms of leukemia in animals, causes of leukemia in humans are to a large extend unknown. *The Merck Manual* 1233 (16$^{th}$ ed. 1992). Transformation to malignancy typically occurs in a single cell through two or more steps with subsequent proliferation and clonal expansion. In some leukemias, specific chromosomal translocations have been identified with consistent leukemic cell morphology and special clinical features (e.g., translocations of 9 and 22 in chronic myelocytic leukemia, and of 15 and 17 in acute promyelocytic leukemia). Acute leukemias are predominantly undifferentiated cell populations and chronic leukemias more mature cell forms.

Acute leukemias are divided into lymphoblastic (ALL) and non-lymphoblastic (ANLL) types. They may be further subdivided by their morphologic and cytochemical appearance according to the French-American-British (FAB) classification or according to their type and degree of differentiation. The use of specific B- and T-cell and myeloid-antigen monoclonal antibodies are most helpful for classification. ALL is predominantly a childhood disease which is established by laboratory findings and bone marrow examination. ANLL, also known as acute myeloblastic leukemia (AML), occurs at all ages and is the more common acute leukemia among adults; it is the form usually associated with irradiation as a causative agent.

Chronic leukemias are described as being lymphocytic (CLL) or myelocytic (CML). CLL is characterized by the appearance of mature lymphocytes in blood, bone marrow, and lymphoid organs. The hallmark of CLL is sustained, absolute lymphocytosis (>5,000/µL) and an increase of lymphocytes in the bone marrow. Most CLL patients also have clonal expansion of lymphocytes with B-cell characteristics. CLL is a disease of older persons. In CML, the characteristic feature is the predominance of granulocytic cells of all stages of differentiation in blood, bone marrow, liver, spleen, and other organs. In the symptomatic patient at diagnosis the total WBC count is usually about 200,000/µL, but may reach 1,000,000/µL. CML is relatively easy to diagnose because of the presence of the Philadelphia chromosome.

The very nature of hematopoietic cancer necessitates using systemic chemotherapy as the primary treatment modality, and radiation therapy may be used as an adjunct to treat local accumulations of leukemic cells. Surgery is rarely indicated as a primary treatment modality, but may be used in managing some complications. Bone marrow transplantation from an HLA-matched sibling is sometimes indicated.

2.7. COLORECTAL CANCERS

In 1999, the incidence of colorectal cancer in the United States was 129,400 cases. In Western countries, cancers of the colon and rectum account for more new cases of cancer than those of any other anatomic site except the lung. *The Merck Manual* 852 (16$^{th}$ ed. 1992). Most colorectal cancers are adenocarcinomas.

Despite the enormous number of deaths attributed to colorectal cancers, their specific mechanism remains unknown. It is known, however, that cancers of the colon and rectum spread in at least five ways: directed extension through the bowel wall; hematogenous metastases; regional lymph node metastases; perineural spread; and intraluminal metastases. Id.

Primary treatment of colorectal cancers typically includes surgery. Many patients, however, must also be treated with a combination of radiation and chemotherapy. As of 1992, the most effective chemotherapy regime consisted of the administration of 5-fluorouracil (5FU) and methyl-CCNU. Id.

2.8. TOPOISOMERASE INHIBITORS

Topoisomerases are enzymes that catalyze the relaxation of negatively supercoiled deoxyribonucleic acid (DNA). The process they catalyze is believed to comprise three steps: cleavage of one or both strands of a supercoiled DNA; passage of a segment of DNA through the break that is formed; and resealing of the break. Type I topoisomerases cleave one strand of DNA; type II topoisomerases cleave both strands. Stryer, L., *Biochemistry* 662-663 (3$^{rd}$ ed., 1988).

Because supercoiled double-stranded DNA must be unwound before processes such as replication, recombination, and transcription can occur, inhibition of the unwinding process can have dramatic consequences. For example, compounds that prevent or slow topoisomerase activity can be used to prevent cell growth and/or cause cell death. Such compounds, which are referred to as "topoisomerase inhibitors," have thus shown promise in the treatment of various types of cancer. Camptothecin and its analogues are examples of topoisomerase inhibitors that exert their effect by stabilizing DNA-topoisomerase I complexes, thereby leaving an irreversible break in the double-stranded DNA with which they are associated. Avgeropoulos, N. G., and Batchelor, T. T., *The Oncologist* 4:209-224 (1999).

A specific camptothecin analogue is irinotecan (also referred to as CPT-11), which is chemically named (4S)-4,11-diethyl-4-hydroxy-9-[(4-piperidino-piperidino)carbonyl-oxy]1H-pyranol-[3',4':6,7]indolizinol[1,2-b]quinoline-3,14-(4H,12H)dione and is described in U.S. Pat. No. 4,604,463. The hydrochloride trihydrate of irinotecan is sold under the tradename CAMPTOSAR®, and is indicated in the United States for the treatment of patients with metastatic carcinoma of the colon or rectum that recurred or progressed following 5-fluorouracil based therapy. *Physicians' Desk Reference*, 2412-2418 (54$^{th}$ ed., 2000). It has also recently been approved in the United States as a first-line therapy to treat patients with metastic colorectal cancer in combination with 5-fluorouracil and leucovorin. Irinotecan has also reportedly been used to treat other cancers, such as malignant gliomas and NSCLC. See, e.g., Avgeropoulos, N. G., and Batchelor, T. T., *The Oncologist* 4:209-224 (1999).

Like other topoisomerase inhibitors, irinotecan and its metabolites (e.g., SN-38) have numerous adverse effects. Examples of such adverse effects include, but are not limited to, early and late-forming diarrhea, nausea, vomiting, anorexia, constipation, flatulence, leukopenia, anemia, neutropenia, asthenia, abdominal cramping, fever, pain, loss of body weight, dehydration, alopecia, dyspnea, insomnia, and dizziness. See, e.g., *Physicians' Desk Reference*, 2415 (54$^{th}$ ed., 2000). The mechanisms by which these undesired effects occur are not well understood, but are believed to be different. In particular, the early and late-forms of diarrhea typically experienced by patients are reportedly mediated by different mechanisms. Id. But whatever their cause, the severity of one or more of their adverse effects limits the amount of topoisomerase inhibitors that can be administered to patients. The effectiveness of topoisomerase inhibitors such as irinotecan is consequently limited not only by their ability to inhibit topoisomerase activity, but also by the severity and nature of their adverse effects.

Attempts have been made to alleviate adverse effects associated with irinotecan. For example, loperamide and the combination of loperamide and acetorphan have reportedly been administered to patients in an effort to reduce delayed-onset diarrhea. Rothenberg, M. L., *Annals of Oncology* 8:837-855 (1997). Unfortunately, these attempts met with limited success. Id.

2.9. THALIDOMIDE

Thalidomide is a racemic compound sold under the tradename THALOMID® and chemically named α-(N-phthalimido)glutarimide or 2-(2,6-dioxo-3-piperidinyl)-1H-isoindole-1,3(2H)-dione. Thalidomide was originally developed in the 1950's to treat morning sickness, but due to its tetragenic effects was withdrawn from use. Thalidomide is now indicated in the United States for the acute treatment of the cutaneous manifestations of erythema nodosum leprosum. *Physicians' Desk Reference*, 911-916 (54$^{th}$ ed., 2000). Because its administration to pregnant women can cause birth defects, the sale of thalidomide is strictly controlled. Id.

In addition to treating symptoms of leprosy, thalidomide has reportedly been used to treat chronic graft-vs-host disease, rheumatoid arthritis, sarcoidosis, several inflammatory skin diseases, and inflammatory bowel disease. See generally, Koch, H. P., *Prog. Med. Chem.* 22:165-242 (1985). See also, Moller, D. R., et al., *J. Immunol.* 159:5157-5161 (1997); Vasiliauskas, E. A., et al., *Gastroenterology* 117:1278-1287 (1999); and Ehrenpreis, E. D., et al., *Gastroenterology* 117:1271-1277 (1999). It has further been alleged that thalidomide can be combined with other drugs to treat iscehemia/reperfusion associated with coronary and cerebral occlusion. See U.S. Pat. No. 5,643,915, which is incorporated herein by reference.

Thalidomide has also reportedly been clinically investigated in the treatment of specific types of cancers. These include refractory multiple myeloma, brain, melanoma, breast, colon, mesothelioma, and renal cell carcinoma. See, e.g., Singhal, S., et al., *New England J. Med.* 341(21):1565-1571 (1999); and Marx, G. M., et al., *Proc. Am. Soc. Clin. Oncology* 18:454a (1999). It has further been reported that thalidomide can be used to prevent the development of chronic cardiomyopathy in rats caused by doxorubicin. Costa, P. T., et al., *Blood* 92(10:suppl. 1):235b (1998). Other reports concerning the use of thalidomide in the treatment of specific cancers include its combination with carboplatin in the treatment of glioblastoma multiforme. McCann, J., *Drug Topics* 41-42 (Jun. 21, 1999). Thalidomide has reportedly also been used as an antiemetic during the treatment of astrocytoma. Zwart, D., Arzneim.-Forsch. 16(12):1688-1689 (1966).

If there is a general mechanism by which thalidomide aids in the treatment of some cancers, its nature remains unclear. See, e.g., Moreira, A. L., et al., *J. Expr. Med.* 177:1675-1680 (1993); McHugh, S. M., et al., *Clin. Exper. Immunol.* 99:160-167 (1995); and Moller, D. R., et al., *J. Immunol.* 159:5157-5161 (1997). It has been reported, however, that thalidomide is an antiangiogenic agent that can suppress tumor necrosis factor α (TNF-α) and interleukin 12 (IL-12) production. See, e.g., Moller, D. R., et al., *J. Immunol.* 159:5157-5161 (1997); Moreira, A. L., et al., *J. Exp. Med.* 177:1675-1680 (1993); U.S. Pat. Nos. 5,593,990, 5,629,327, and 5,712,291 to D'Amato and U.S. Pat. No. 5,385,901 to Kaplan. And in vitro studies suggest that thalidomide affects the production of a variety of other proteins. See, e.g., McHugh, S. M., et al., *Clin. Exp. Immunol.* 99:160-167 (1995). Thalidomide may also affect mechanisms related to epithelial or endothelial function or growth. D'amato M., et al., *Proc. Natl. Acad. Sci.* 91:4082-4085(1994).

Given the great need for an effective and safe treatment of cancer, there continues to be an extensive amount of research on new drugs or ways of improving existing therapies. This invention addresses the need for a safe and effective cancer treatment.

3. SUMMARY OF THE INVENTION

This invention is directed to pharmaceutical compositions, pharmaceutical dosage forms, kits, methods of treating or preventing cancer, methods of reducing or avoiding adverse effects associated with chemotherapy and radiation therapy, and methods of improving the tolerance of patients to chemotherapy and radiation treatment.

A first embodiment of the invention encompasses a method of treating primary and/or metastatic cancer, which comprises administering to a patient in need of such treatment a therapeutically effective amount of a topoisomerase inhibitor, or a pharmaceutically acceptable prodrug, salt, solvate, hydrate, or clathrate thereof, and a therapeutically effective amount of thalidomide, or a pharmaceutically acceptable prodrug, salt, solvate, hydrate, or clathrate thereof.

Specific examples of cancers that can be treated by this method include, but are not limited to, cancer of the head, neck, eye, mouth, throat, esophagus, chest, bone, lung, colon, rectum, stomach, prostate, breast, ovaries, kidney, liver, pancreas, and brain. A specific cancer that can be treated by this method is metastatic colorectal cancer.

A second embodiment of the invention encompasses a method of increasing the dosage of a topoisomerase inhibitor that can be safely and effectively administered to a patient, which comprises administering to a patient in need of such an increased dosage an amount of thalidomide, or a pharmaceutically acceptable prodrug, salt, solvate, hydrate, or clathrate thereof, that is sufficient to reduce a dose-limiting adverse effect associated with the topoisomerase inhibitor. In a preferred method of this embodiment, thalidomide is administered orally and daily in an amount of from about 1 to about 2000 mg, preferably from about 50 to about 1000 mg, more preferably from about 100 to 750 mg, and most preferably from about 200 to about 500 mg.

Examples of dose-limiting adverse effects associated with topoisomerase inhibitors include, but are not limited to: gastrointestinal toxicity such as, but not limited to, early and late-forming diarrhea and flatulence; nausea; vomiting; anorexia; leukopenia; anemia; neutropenia; asthenia; abdominal cramping; fever; pain; loss of body weight; dehydration; alopecia; dyspnea; insomnia; dizziness, mucositis, xerostomia, and kidney failure. Specific dose-limiting adverse effects are early-forming diarrhea and late-forming diarrhea.

A third embodiment of the invention encompasses a method of reducing or preventing an adverse effect associated with chemotherapy or radiation therapy, which comprises administering to a patient in need of such treatment or prevention an amount of thalidomide, or a pharmaceutically acceptable prodrug, salt, solvate, hydrate, or clathrate thereof, that is sufficient to reduce an adverse effect associated with the chemotherapy or radiation therapy. This embodiment includes the use of thalidomide to protect against or treat an adverse effect associated with the use of chemotherapy or radiation therapy. The use of the thalidomide in this embodiment encompasses raising a patient's tolerance for chemotherapy or radiation therapy. In a preferred method of this embodiment, thalidomide is administered orally and daily in an amount of from about 1 to about 2000 mg, preferably from about 50 to about 1000 mg, more preferably from about 100 to 750 mg, and most preferably from about 200 to about 500 mg.

Examples of adverse effects associated with chemotherapy and radiation therapy include, but are not limited to: gastrointestinal toxicity such as, but not limited to, early and late-forming diarrhea and flatulence; nausea; vomiting; anorexia; leukopenia; anemia; neutropenia; asthenia; abdominal cramping; fever; pain; loss of body weight; dehydration; alopecia; dyspnea; insomnia; dizziness, mucositis, xerostomia, and kidney failure.

A fourth embodiment of the invention encompasses a method of increasing the therapeutic efficacy of a topoisomerase inhibitor which comprises administering to a patient in need of such increased therapeutic efficacy an amount of thalidomide, or a pharmaceutically acceptable prodrug, salt, solvate, hydrate, or clathrate thereof, that is sufficient to increase the therapeutic efficacy of the topoisomerase inhibitor.

A fifth embodiment of the invention encompasses a pharmaceutical composition comprising a topoisomerase inhibitor, or a pharmaceutically acceptable prodrug, salt, solvate, hydrate, or clathrate thereof, and thalidomide, or a pharmaceutically acceptable prodrug, salt, solvate, hydrate, or clathrate thereof.

A sixth embodiment of the invention encompasses a dosage form comprising a topoisomerase inhibitor, or a pharmaceutically acceptable prodrug, salt, solvate, hydrate, or clathrate thereof, and thalidomide, or a pharmaceutically acceptable prodrug, salt, solvate, hydrate, or clathrate thereof.

A seventh embodiment of the invention encompasses a kit for use in the treatment or prevention of cancer which comprises a parenteral dosage form of irinotecan, or a pharmaceutically acceptable prodrug, salt, solvate, hydrate, or clathrate thereof, and an oral dosage form of thalidomide, or a pharmaceutically acceptable prodrug, salt, solvate, hydrate, or clathrate thereof.

Examples of topoisomerase inhibitors that can be used in the methods, compositions, and kits of the invention include, but are not limited to, camptothecin, iriniotecan, SN-38, topotecan, 9-aminocamptothecin, GG-211, DX-8951f, saintopin, UCE6, UCE1022, TAN-1518A, TAN-1518B, KT6006, KT6528, ED-110, NB-506, ED-110, NB-506, rebeccamycin, bulgarein, Hoescht dye 33342, Hoechst dye 33258, nitidine, fagaronine, epiberberine, coralyne, beta-lapachone, BC-4-1, IST-622, rubitecan, pyrazoloacridine, XR-5000, and pharmaceutically acceptable prodrugs, salts, solvates, clathrates, hydrates, and metabolites thereof. Preferred topoisomerase inhibitors include, but are not limited to, irinotecan, SN-38, and pharmaceutically acceptable prodrugs, salts, solvates, hydrates, and clathrates thereof. In certain embodiments, the topoisomerase inhibitor is other than irinotecan.

3.1. DEFINITIONS

As used herein, the term "cancer" includes but is not limited to solid tumors and blood born tumors. The term cancer refers to disease of skin tissues, organs, bone, cartilage, blood and vessels. The invention encompasses the treatment of various types of cancer including but not limited to cancer of the head, neck, eye, mouth, throat, esophagus, chest, bone, lung, colon, rectum, stomach, prostate, breast, ovaries, kidney, liver, pancreas, and brain. The term "cancer" further encompasses primary and metastatic cancers, unless otherwise indicated.

As used herein to describe a compound or chemical moiety, the term "derivative" means a compound or chemical moiety wherein the degree of saturation of at least one bond has been changed (e.g., a single bond has been changed to a double or triple bond) or wherein at least one hydrogen atom is replaced with a different atom or a chemical moiety. Examples of different atoms and chemical moieties include, but are not limited to, halogen, oxygen, nitrogen, sulfur, hydroxy, methoxy, alkyl, amine, amide, ketone, and aldehyde.

As used herein, the term "prodrug" means a derivative of a compound that can hydrolyze, oxidize, or otherwise react under biological conditions (in vitro or in vivo) to provide the compound. Examples of prodrugs include, but are not limited to, derivatives of topoisomerase inhibitors or thalidomide that comprise biohydrolyzable moieties such as biohydrolyzable amides, biohydrolyzable esters, biohydrolyzable carbamates, biohydrolyzable carbonates, and biohydrolyzable ureides.

As used herein, the terms "biohydrolyzable carbamate," "biohydrolyzable carbonate," and "biohydrolyzable ureide" mean a carbamate, carbonate, or ureide, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, the term "biohydrolyzable ester" means an ester of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters.

As used herein, the term "biohydrolyzable amide" means an amide of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable amides include, but are not limited to, lower alkyl amides, α-amino acid amides, alkoxyacyl amides, and alkylaminoalkylcarbonyl amides.

As used herein, the term "pure diastereomer" means a composition that comprises one diastereomer of a compound and is substantially free of other diastereomers of the compound. A typically pure diastereomer is a compound comprising greater than about 80% by weight of one diastereomer of a compound and less than about 20% by weight of other diastereomers of the compound, more preferably greater than about 90% by weight of one diastereomer of a compound and less than about 10% by weight of other diastereomers of the compound, even more preferably greater than about 95% by weight of one diastereomer of a compound and less than about 5% by weight of other diastereomers of the compound, and most preferably greater than about 99% by weight of one diastereomer of a compound and less than about 1% by weight of other diastereomers of the compound.

As used herein, the terms "optically pure," "pure enantiomer," and "optically pure enantiomer" mean a composition that comprises one enantiomer of a compound and is substantially free of the opposite enantiomer of the compound. A typical optically pure enantiomers is a composition comprising greater than about 80% by weight of one enantiomer of a compound and less than about 20% by weight of the opposite enantiomer of the compound, more preferably greater than about 90% by weight of one enantiomer of a compound and less than about 10% by weight of the opposite enantiomer of the compound, even more preferably greater than about 95% by weight of one enantiomer of a compound and less than about 5% by weight of the opposite enantiomer of the compound, and most preferably greater than about 99% by weight of one enantiomer of a compound and less than about 1% by weight of the opposite enantiomer of the compound.

4. DETAILED DESCRIPTION OF THE INVENTION

This invention encompasses pharmaceutical compositions, pharmaceutical dosage forms, kits, methods of treating diseases or conditions such as cancer, methods of preventing metastases, methods of improving the therapeutic profile of anti-cancer drugs, and methods of reducing or avoiding adverse effects associated with chemotherapy and radiation therapy.

This invention is based, in part, on the ability of thalidomide to: (1) treat cancer; (2) improve the efficacy or tolerability of other chemotherapeutic or radiation therapies for cancer, or; (3) lessen the severity of certain dose-limiting toxicities of other anti-cancer drugs. Embodiments of the invention include a method of treating or preventing cancer which comprises the administration of thalidomide, or a derivative, analogue, pharmaceutically acceptable prodrug, salt, solvate, hydrate, or clathrate thereof, in combination with at least one other anti-cancer drug to a patient. Another embodiment of the invention encompasses a method of reducing or avoiding adverse effects associated with an anti-cancer drug, which comprises administering thalidomide, or a derivative, analogue, pharmaceutically acceptable prodrug, salt, solvate, hydrate, or clathrate thereof to a patient. Examples of other anti-cancer drugs that can be used in methods of the invention include, but are not limited to, taxol (paclitaxel), taxotere (docetaxel), doxorubicin, cisplatin, topoisomerase inhibitors, and other drugs described herein (e.g., those described below in Section 4.1.1.). In one embodiment, the most preferred anti-cancer drugs are topoisomerase inhibitors. Other embodiments of the invention encompass pharmaceutical compositions, pharmaceutical dosage forms, and kits comprising thalidomide, or a derivative, analogue, pharmaceutically acceptable prodrug, salt, solvate, hydrate, or clathrate thereof, and at least one other anti-cancer drug.

This invention further encompasses methods of: 1) allowing the completion of chemotherapy in a greater percentage of patients; 2) avoiding deterioration of patients' nutritional status secondary to gastrointestinal toxicity; and 3) improving the overall quality of patients' life during chemotherapy.

Preferred embodiments of the invention are based on the unique ability of thalidomide to improve the overall therapeutic profile of topoisomerase inhibitors when used in the treatment or prevention of various primary or metastatic cancers. For example, thalidomide as used in this invention can improve the efficacy of topoisomerase inhibitors at their common or approved doses. Thalidomide can further be used in combination with lower doses of topoisomerase inhibitors to reduce or avoid adverse affects associated with them while maintaining their efficacy. Thalidomide can also be used in methods of this invention to reduce or avoid adverse effects that are associated with the administration of topoisomerase inhibitors. Indeed, a preferred use of thalidomide is to reduce or avoid intolerance of topoisomerase inhibitors so that they can be used in greater amounts in the treatment of cancer. And a specific embodiment of the invention encompasses the use of thalidomide to reduce or avoid gastrointestinal toxicity caused by topoisomerase inhibitors. In short, this invention encompasses therapeutic effects that result from an unexpected and unique synergy between thalidomide and topoisomerase inhibitors. One of these therapeutic effects is an increased potency or efficacy of topoisomerase inhibitor; another is a reduced toxicity or increased safety of topoisomerase inhibitor.

Compositions of the invention include bulk drug compositions useful in the manufacture of pharmaceutical compositions (e.g., impure or non-sterile compositions), pharmaceutical compositions (i.e., compositions that are suitable for administration to a patient), and individual dosage forms. Each of the compositions and dosage forms of the invention comprise at least two of what are referred to herein as "active ingredients." A first active ingredient is a topoisomerase inhibitor, or a pharmaceutically acceptable prodrug, salt, solvate, hydrate, or clathrate thereof. A second active ingredient is thalidomide, a derivative or analogue of thalidomide, or a pharmaceutically acceptable prodrug, salt, solvate, hydrate, or clathrate thereof.

Examples of topoisomerase inhibitors that can be used in the methods and compositions of the invention include, but are not limited to: camptothecin; irinotecan; SN-38; topotecan; 9-aminocamptothecin; GG-211 (GI 147211); DX-8951f; IST-622; rubitecan; pyrazoloacridine; XR-5000; saintopin; UCE6; UCE1022; TAN-1518A; TAN-1518B; KT6006; KT6528; ED-110; NB-506; ED-110; NB-506; and rebeccamycin; bulgarein; DNA minor groove binders such as, but limited to, Hoescht dye 33342 and Hoechst dye 33258; nitidine; fagaronine; epiberberine; coralyne; beta-lapachone; BC-4-1; and pharmaceutically acceptable salts, solvates, clathrates, and prodrugs thereof. See, e.g., Rothenberg, M. L., *Annals of Oncology* 8:837-855(1997); and Moreau, P., et al., *J. Med. Chem.* 41:1631-1640(1998). Examples of camptothecin derivatives that can be used in the methods and compositions of this invention are disclosed by, for example, U.S. Pat. Nos.: 6,043,367; 6,040,313; 5,932,588; 5,916,896; 5,889,017; 5,801,167; 5,674,874; 5,658,920; 5,646,159; 5,633,260; 5,604,233; 5,597,829; 5,552,154; 5,541,327; 5,525,731; 5,468,754; 5,447,936; 5,446,047; 5,401,747; 5,391,745; 5,364,858; 5,340,817; 5,244,903; 5,227,380; 5,225,404; 5,180,722; 5,122,606; 5,122,526; 5,106,742; 5,061,800; 5,053,512; 5,049,668; 5,004,758; 4,981,968; 4,943,579; 4,939,255; 4,894,456; and 4,604,463, each of which is incorporated herein by reference. Preferred topoisomerase inhibitors include, but are not limited to, irinotecan, SN-38, and pharmaceutically acceptable salts, solvates, clathrates, and prodrugs thereof.

Many topoisomerase inhibitors comprise one or more chiral centers. The methods and compositions of the invention encompass the use of racemic mixtures of such topoisomerase inhibitors, as well as enriched (i.e., uneven) mixtures of their diastereomers or enantiomers, and pure diastereomers or enantiomers of such inhibitors. Pure or substantially pure diastereomers or enantiomers of topoisomerase inhibitors can be prepared by methods well known in the art. These include, but are not limited to, resolution of chiral salts, asymmetric synthesis, or chiral chromatography. See generally, Beesley, T. E. and Scott, R. P. W., *Chiral Chromatography* (John Wiley & Sons, New York: 1999); *Principles of Asymmetric Synthesis,* Gawley, R. E. and Aube, J., eds. (Elsevier, Amsterdam: 1996); *Advanced Asymmetric Synthesis,* Stephenson, G. R., ed. (Chapman & Hall, London: 1996); and *Asymmetric Synthetic Methodology,* Ager, D. R. and East, M. B., eds. (CRC, Boca Raton: 1996). See also, Jacques, J., et al., *Enantiomers, Racemates and Resolutions* (Wiley-Interscience, New York: 1981); Wilen, S. H., et al., *Tetrahedron* 33:2725 (1977); Eliel, E. L. *Stereochemistry of Carbon Compounds* (McGraw-Hill, New York: 1962); and Wilen, S. H., *Tables of Resolving Agents and Optical Resolutions,* 268, Eliel, E. L., ed. (Univ. of Notre Dame Press, Notre Dame: 1972). It is further contemplated that pharmaceutically acceptable prodrugs of topoisomerase inhibitors be used in the methods and compositions of the invention. Physiologically active metabolites of topoisomerase inhibitors disclosed herein as well as those known in the art can also be used in the methods and compositions of the invention. An example of a physiologically active metabolite of a topoisomerase inhibitor is SN-38, which is a metabolite of irinotecan.

Thalidomide contains a chiral center, and is sold as a racemate. The methods and compositions of the invention therefore encompass the use of racemic thalidomide as well as optically pure enantiomers of thalidomide. Optically pure enantiomers of thalidomide can be prepared by methods well known in the art. These include, but are not limited to, resolution of chiral salts, asymmetric synthesis, or chiral chromatography. It is further contemplated that pharmaceutically acceptable prodrugs, salts, solvate, clathrates and derivatives of thalidomide be used in the methods and compositions of the invention. Examples of derivatives of thalidomide that can be used in the methods and compositions of the invention include, but are not limited to, taglutimide, supidimide, EM-12, and those disclosed by International Application WO 94/20085, which is incorporated herein by reference. Other derivatives of thalidomide encompassed by this invention include, but are not limited to, 6-alkyl-2-[3'- or 4'-nitrophthalimido]-glutarimides and 6-alkyl-3-phenylglutarimides. See, e.g., De, A. U., and Pal. D., *J. Pharm. Sci.* 64(2): 262-266 (1975). Preferred thalidomide derivatives are the amino analogues of thalidomide such as amino-thalidomide.

4.1. METHODS OF TREATMENT AND PREVENTION

This invention encompasses methods of treating and preventing a wide variety of disease and conditions in mammals, and in humans in particular. Although dosage forms of the invention can be used in methods of the invention, the active ingredients disclosed herein can be administered separately, in any appropriate form, and by any suitable route.

Without being limited by theory, it is believed that the combined use of a topoisomerase inhibitor and thalidomide to a patient suffering from cancer provides a unique and unexpected synergism. In particular, and without being limited by theory, it is believed that thalidomide can work in combination with a topoisomerase inhibitor to more rapidly kill cancer cells, while at the same time reducing gastrointestinal (e.g., diarrhea) and other side effects associated with chemotherapy (e.g., with topoisomerase inhibitors) and radiation therapy.

Consequently, one embodiment of this invention encompasses methods of treating and/or preventing of cancer. Examples of cancers that can be treated are disclosed herein and include, but are not limited to, primary and metastatic cancer of the head, neck, eye, mouth, throat, esophagus, chest, bone, lung, colon, rectum, stomach, prostate, breast, ovaries, kidney, liver, pancreas, and brain. Specific examples of cancers that can be treated include, but are not limited to: AIDS associated leukemia and adult T-cell leukemia lymphoma; anal carcinoma; astrocytoma; biliary tract cancer; cancer of the bladder, including bladder carcinoma; brain cancer, including glioblastomas and medulloblastomas; breast cancer, including breast carcinoma; cervical cancer; choriocarcinoma; colon cancer including colorectal carcinoma; endometrial cancer; esophageal cancer; Ewing's sarcoma; gastric cancer; gestational trophoblastic carcinoma; glioma; hairy cell leukemia; head and neck carcinoma; hematological neoplasms, including acute and chronic lymphocytic and myelogeneous leukemia; hepatocellular carcinoma; Kaposi's sarcoma; kidney cancer; multiple myeloma; intraepithelial neoplasms, including Bowen's disease and Paget's disease; liver cancer; lung cancer including small cell carcinoma; lymphomas, including Hodgkin's disease, lymphocytic lymphomas, non-Hodgkin's lymphoma, Burkitt's lymphoma, diffuse large cell lymphoma, follicular mixed lymphoma, and lymphoblastic lymphoma; lymphocytic leukemia; neuroblastomas; oral cancer, including squamous cell carcinoma; ovarian cancer, including those arising from epithelial cells, stromal cells, germ cells and mesenchymal cells; pancreatic cancer; prostate cancer; rectal cancer; sarcomas, including soft tissue sarcomas, leiomyosarcoma, rhabdomyosarcoma, liposcarcoma, fibrosarcoma, and osteosarcoma; skin cancer, including melanoma, Kaposi's sarcoma, basal cell cancer and squamous cell cancer; testicular cancer, including testicular carcinoma and germinal tumors (e.g., semicoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilm's tumor.

The invention encompasses methods of treating of patients with primary and metastatic cancers. It further encompasses methods of treating patients who have been previously treated for cancer, as well as those who have not previously been treated for cancer. Indeed, the methods and compositions of this invention can be used in first-line and second-line cancer treatments. In a specific embodiment of the invention, the cancer is metastatic. In another specific embodiment, the patient having a cancer is immunosuppressed by reason of having previously undergone anti-cancer therapy (e.g., chemotherapy radiation). In a preferred embodiment, thalidomide is administered to a patient undergoing topoisomerase treatment before any adverse effect or intolerance occurs.

Other embodiments of the invention include methods of increasing the dosage of a topoisomerase inhibitor that can be safely and effectively administered to a patient, and methods of varying the dosage cycle used to administer a topoisomerase inhibitor to a patient while avoiding dose-limiting toxicities.

Another embodiment of the invention described in detail encompasses a method of reducing, treating and/or preventing adverse, or undesired, effects associated with chemotherapy and/or radiation therapy.

4.1.1. METHODS OF TREATING AND/OR PREVENTING CANCER

The methods of treating and/or preventing cancer encompassed by this invention comprise administering at least two drugs (also referred to herein as "active ingredients" or "active agents") to a patient (e.g., a human) suffering, or likely to suffer, from cancer: 1) an anti-cancer drug and; 2) thalidomide, a derivative or analogue of thalidomide, or a pharmaceutically acceptable salt, solvate, clathrate, hydrate, or prodrug thereof. Preferred anti-cancer drugs are topoisomerase inhibitors, or pharmaceutically acceptable salts, solvates, clathrates, hydrates, and prodrugs thereof. The two active ingredients can be administered concurrently, sequentially, and by the same or by different routes of administration. For example, one active ingredient (e.g., thalidomide) can be administered to a patient prior to, during, or after the administration of the other active ingredient.

A preferred method of the invention comprises the administration of: 1) a topoisomerase inhibitor, or a pharmaceutically acceptable prodrug, salt, solvate, hydrate, or clathrate thereof; 2) thalidomide, or a pharmaceutically acceptable derivative, prodrug, salt, solvate, hydrate, or clathrate thereof; and 3) radiation therapy. Administration of each of the drugs can occur prior to, during, or after radiation therapy.

Another embodiment of the invention encompasses a method of treating cancer which comprises the administration of at least three active ingredients simultaneously or sequentially: 1) a topoisomerase inhibitor, or a pharmaceutically acceptable prodrug, salt, solvate, hydrate, or clathrate thereof; 2) thalidomide, or a pharmaceutically acceptable derivative, prodrug, salt, solvate, hydrate, or clathrate thereof; and 3) an additional anti-cancer drug.

Examples of anti-cancer drugs that can be used in the various embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; pirozantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine;

betaciamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin, pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras famesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. These two agents are particularly useful when used in methods employing thalidomide and a topoisomerase inhibitor.

The magnitude of a prophylactic or therapeutic dose of each active ingredient in the acute or chronic management of cancer will typically vary with the specific active ingredients, the severity and type of cancer, and the route of administration. The dose, and perhaps the dose frequency, may also vary according to age, body weight, response, and the past medical history of the patient. Suitable dosing regimens can be readily selected by those skilled in the art with due consideration of such factors by following, for example, dosages reported in the literature and recommended in the *Physician's Desk Reference® (54$^{th}$ ed., 2000).*

Unless otherwise indicated, the magnitude of a prophylactic or therapeutic dose of each active ingredient used in an embodiment of the invention will be that which is known to those in the art to be safe and effective, or is regulatory approved.

In one embodiment of the invention, the topoisomerase inhibitor irinotecan is administered parenterally about every three weeks in an amount of from about 1 to about 1000 mg/m², preferably in an amount of from about 25 to about 750 mg/m², more preferably in an amount of from about 50 to about 500 mg/m², and most preferably in an amount of from about 100 to about 350 mg/m². And in one embodiment of the invention, thalidomide is administered orally and daily in an amount of from about 1 to about 2000 mg, preferably from about 50 to about 1000 mg, more preferably from about 100 to 750 mg, and most preferably from about 200 to about 500 mg.

As noted elsewhere herein, this invention encompasses a method of reducing the time between therapeutically safe and effective doses of anti-cancer drugs (e.g., topoisomerase inhibitors). Consequently, in one specific embodiment of the invention, irinotecan is administered in a cycle of less than about three weeks (e.g., about once every two weeks, about once every ten days, or about once every week). The invention further allows the frequency, number, and length of anti-cancer drug dosing cycles to be increased. Thus, another specific embodiment of the invention encompasses the administration of irinotecan for more cycles than are typical when it is administered alone. See, e.g., *Physicians' Desk Reference*, 2412-2418 (54$^{th}$ ed., 2000). In yet another specific embodiment of the invention, irinotecan is administered for a greater number of cycles that would typically cause dose-limiting toxicity in a patient to whom thalidomide is not also being administered.

In a typical embodiment of the invention, a topoisomerase inhibitor is administered by intravenous infusion over about 90 minutes every cycle. In a specific embodiment wherein the topoisomerase inhibitor is irinotecan, one cycle comprises the administration of about 125 mg/m² irinotecan on days 1, 8, 15, and 22, and then two weeks of rest. In another specific embodiment, each cycles comprises the administration of about 350 mg/m² of irinotecan, followed by three weeks of rest. Typically, the number of cycles during which a topoisomerase inhibitor such as irinotecan is administered to a patient will be from about 1 to about 12 cycles, more typically from about 2 to about 10 cycles, and even more typically from about 2 to about 8 cycles.

The dosage amounts and frequencies provided above are encompassed by the terms "therapeutically effective," "prophylactically effective," and "therapeutically or prophylactically effective" as used herein. When used in connection with an amount of a thalidomide or thalidomide derivative, these terms further encompass an amount of thalidomide or thalidomide derivative that reduces, prevents, or eliminates an adverse effect associated with the administration of radiation or an anti-cancer drug such as a topoisomerase inhibitor, or an amount that otherwise improves the efficacy of radiation therapy or of an anti-cancer drug in the treatment or prevention of cancer.

The suitability of a particular route of administration employed for a particular active ingredient will depend on the active ingredient itself (e.g., whether it can be administered orally without decomposing prior to entering the blood stream) and the disease being treated. For example, treatment of tumors on the skin or on exposed mucosal tissue may be more effective if one or both active ingredients are administered topically, transdermally, or mucosally (e.g., by nasal, sublingual, buccal, rectal, or vaginal administration). Treatment of tumors within the body, or prevention of cancers that may spread from one part of the body to another, may be more effective if one or both of the active ingredients are administered parenterally or orally. Similarly, parenteral administration may be preferred for the acute treatment of a disease, whereas transdermal or subcutaneous routes of administration may be employed for chronic treatment or prevention of a disease.

4.1.2. METHODS OF INCREASING ANTI-CANCER DRUG DOSAGES

This invention encompasses a method of increasing the dosage of an anti-cancer drug, such as a topoisomerase inhibitor, that can be safely and effectively administered to a patient. This method comprises administering to a patient (e.g., a human) thalidomide, or a pharmaceutically acceptable derivative, salt, solvate, clathrate, hydrate, or prodrug thereof. Patients that can benefit by this method are those likely to suffer from an adverse effect associated with an anti-cancer drug that is alleviated or reduced by the administration of thalidomide, or a pharmaceutically acceptable derivative, salt, solvate, clathrate, hydrate, or prodrug thereof, and which is of such severity that it would otherwise limit the amount of topoisomerase inhibitor that can be safely and effectively administered to them. Such adverse effects are referred to herein as "dose-limiting."

For example, adverse effects that are associated with topoisomerase inhibitors and which can limit the amount of a topoisomerase inhibitor that can safely and effectively be administered to a patient include, but are not limited to: gastrointestinal toxicity such as, but not limited to, early and late-forming diarrhea and flatulence; nausea; vomiting; anorexia; leukopenia; anemia; neutropenia; asthenia; abdominal cramping; fever; pain; loss of body weight; dehydration; alopecia; dyspnea; insomnia; dizziness, mucositis, xerostomia, and kidney failure.

According to a specific method of the invention, thalidomide, or a pharmaceutically acceptable derivative, salt, solvate, clathrate, hydrate, or prodrug thereof, is administered prior to, during, or after a topoisomerase inhibitor. In one embodiment, thalidomide is administered orally and daily in an amount of from about 1 to about 2000 mg, preferably from about 50 to about 1000 mg, more preferably from about 100 to 750 mg, and most preferably from about 200 to about 500 mg.

4.1.3. METHODS OF TREATING AND/OR PREVENTING ADVERSE EFFECTS ASSOCIATED WITH CHEMOTHERAPY AND RADIATION THERAPY

As discussed elsewhere herein, this invention encompasses a method of treating and/or preventing adverse effects associated with chemotherapy and/or radiation therapy, such as that administered to patients with cancer. This method comprises administering to a patient (e.g., a human) thalidomide, or a pharmaceutically acceptable derivative, salt, solvate, clathrate, hydrate, or prodrug thereof before, during, or after the occurrence of the adverse effect.

Examples of adverse effects associated with chemotherapy and radiation therapy that can be treated or prevented by this method include, but are not limited to: gastrointestinal toxicity such as, but not limited to, early and late-forming diarrhea and flatulence; nausea; vomiting; anorexia; leukopenia; anemia; neutropenia; asthenia; abdominal cramping; fever; pain; loss of body weight; dehydration; alopecia; dyspnea; insomnia; dizziness, mucositis, xerostomia, and kidney failure.

According to this method, thalidomide, or a pharmaceutically acceptable derivative, salt, solvate, clathrate, hydrate, or prodrug thereof, is administered prior to, during, or after chemotherapy or radiation therapy. In one embodiment of this method, thalidomide is administered prior to the administration of a topoisomerase inhibitor or radiation therapy. In another embodiment, thalidomide is administered during or after the administration of a topoisomerase inhibitor or radiation therapy. In still another embodiment, thalidomide is administered at least twice for each treatment with a topoisomerase inhibitor or radiation therapy; e.g., once during the treatment and at least once following the treatment, once prior to the treatment and once during the treatment, once both prior to and at least once after the treatment, or combinations thereof. Preferably, thalidomide is administered before any adverse event or symptom occurs. Indeed, thalidomide can be administered to a patient prior to the administration of chemotherapy and/or radiation therapy, in which case it can be considered as a protectant.

In a specific embodiment of this method, thalidomide is administered in an amount of from about 1 to about 2000 mg, preferably from about 50 to about 1000 mg, more preferably from about 100 to 750 mg, and most preferably from about 200 to about 500 mg orally and daily following radiation therapy or the administration of an anti-cancer drug such as, but not limited to, a topoisomerase inhibitor.

4.2. PHARMACEUTICAL COMPOSITIONS AND DOSAGE FORMS

Pharmaceutical compositions can be used in the preparation of individual dosage forms. Consequently, pharmaceutical compositions and dosage forms of the invention comprise the active ingredients disclosed herein (e.g., a topoisomerase inhibitor, or a pharmaceutically acceptable prodrug, salt, solvate, hydrate, or clathrate thereof, and thalidomide, a derivative or analogue of thalidomide, or a pharmaceutically acceptable prodrug, salt, solvate, hydrate, or clathrate thereof). Pharmaceutical compositions and dosage forms of the invention can further comprise one or more excipients.

Pharmaceutical compositions and dosage forms of the invention can also comprise one or more additional active ingredients. Examples of optional additional active ingredients include, but are not limited to, leucovorin, 5-flurouracil, and mixtures thereof.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, this invention encompasses pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions of the invention can comprise excipients that are well known in the art and are listed, for example, in the U.S. Pharmocopia (USP) SP (XXI)/NF (XVI). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability. Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise thalidomide, a derivative or analogue of thalidomide, or a pharmaceutically acceptable salt, solvate, clathrate, hydrate, or prodrug thereof in an amount of from about 1 mg to about 2000 mg, more preferably from about 50 mg to about 1000 mg, even more preferably from about 100 mg to about 750 mg, and most preferably from about 200 mg to about 500 mg. Similarly, typical dosage forms of the invention comprise a topoisomerase inhibitor or a pharmaceutically acceptable salt, solvate, clathrate, hydrate, prodrug or derivative thereof in an amount of from about 1 mg to about 1000 mg, more preferably from about 25 mg to about 750 mg, even more preferably from about 50 mg to about 500 mg, and most preferably from about 100 mg to about 350 mg.

4.2.1. ORAL DOSAGE FORMS

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences*, 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the invention comprises thalidomide, anhydrous lactose, microcrystalline cellulose, polyvinylpyrrolidone, stearic acid, colloidal anhydrous silica, and gelatin.

4.2.2. DELAYED RELEASE DOSAGE FORMS

Active ingredients of the invention can be administered by controlled release means or by delivery devices that are well known to those of ordinary skill in the art. Examples include, but are not limited to, those described in U.S. Pat. Nos.: 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.2.3. PARENTERAL DOSAGE FORMS

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention. For example, cyclodextrin and its derivatives can be used to increase the solubility of thalidomide and its derivatives. See, e.g., U.S. Pat. No. 5,134,127, which is incorporated herein by reference.

A preferred parenteral composition of the invention is intended for dilution with 5% Dextrose Injection, USP, or 0.9% Sodium Chloride Injection, USP, prior to administration to a patient, and is an aqueous solution that comprises irinotecan, sorbitol NF powder, and lactic acid, USP, and has a pH of from about 3.0 to about 3.8.

4.2.4. TRANSDERMAL, TOPICAL, AND MUCOSAL DOSAGE FORMS

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences,* 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

4.2.5. KITS

Typically, active ingredients of the invention are preferably not administered to a patient at the same time or by the same route of administration. This invention therefore encompasses kits which, when used by the medical practitioner, can simplify the administration of appropriate amounts of active ingredients to a patient.

A typical kit of the invention comprises a dosage form of an anti-cancer drug (e.g., a topoisomerase inhibitor) or a pharmaceutically acceptable prodrug, salt, solvate, hydrate, or clathrate thereof, and a dosage form of thalidomide, or a pharmaceutically acceptable derivative, prodrug, salt, solvate, hydrate, or clathrate thereof. Kits encompassed by this invention can further comprise additional active ingredients. Examples of optional additional active ingredients include, but are not limited to, leucovorin, 5-flurouracil, and mixtures thereof.

Kits of the invention can further comprise devices that are used to administer the active ingredients. Examples of such devices include, but are not limited to, syringes, drip bags, patches, and inhalers.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

A specific kit of the invention comprises a solid dosage form of thalidomide suitable for oral administration to a patient, and a liquid dosage form of irinotecan suitable for dilution and parenteral administration to a patient. A preferred oral dosage form of thalidomide comprises 50 mg thalidomide, anhydrous lactose, microcrystalline cellulose, polyvinylpyrrolidone, stearic acid, colloidal anhydrous silica, and gelatin. A preferred liquid dosage form of irinotecan comprises 100 mg irinotecan hydrochloride, sorbitol NF powder, and lactic acid, USP, and has a pH of from about 3.0 to about 3.8.

Other kits encompassed by the invention will be readily apparent to those skilled in the art, since thalidomide, irinotecan, and other therapeutic and anti-cancer drugs or radiation therapies are well known and/or commercially available.

5. EXAMPLES

Certain embodiments of the invention, as well as certain novel and unexpected advantages of the invention, are illustrated by the following non-limiting examples.

5.1. Example 1: Treatment of Colorectal Cancer

A pilot clinical trial was conducted to investigate the safety and efficacy of administering thalidomide (400 mg/day, administered at bedtime) and irinotecan (325-350 mg/m$^2$ every 21 days) to patients with metastatic colorectal cancer. An interim analysis performed after enrollment of the first 9 patients on this protocol (2-8 cycles of irinotecan) revealed a remarkable absence of gastrointestinal toxicity typically associated with irinotecan. See Table 1. All patients were able to complete the prescribed chemotherapy regimen; only one patient required a 50% reduction of the irinotecan dose due to asthenia, and only one patient required a thalidomide dose reduction by 75% due to somnolence. Of the seven patients that could be evaluated, one went into complete remission, two attained partial remission, one had stable disease, and three progressed.

TABLE 1

Observed Toxicity Profile for Combination Therapy with Thalidomide and Irinotecan in 9 Patients with Metastatic Colorectal Cancer Compared with the Expected Toxicity Profile of Irinotecan Monotherapy

| Symptom | Expected (%) | | Observed (N) | | |
|---|---|---|---|---|---|
| | Grade 1-4 | Grade 3-4 | Grade 1-4 | Grade 3-4 | p |
| Nausea | 86.2 | 16.8 | 0 | 1 | <0.00001 |
| Vomiting | 66.8 | 12.5 | 0 | 0 | 0.00005 |
| Diarrhea (Late) | 87.8 | 30.6 | 1 | 0 | <0.00001 |
| Abdominal colic/pain | 23.7 | 2.3 | 0 | 0 | n.s |
| Constipation | 29.9 | 2.0 | 4 | 0 | n.s. |
| Asthenia | 75.7 | 12.2 | 6 | 0 | n.s. |

The p-values shown in Table 1 refer to the probability of observing the specified number of Grade 1-4 symptoms among 9 patients, given the expected frequencies of Grade 1-4 toxicity. Expected frequencies of toxicity were obtained from Rothenberg, M. L., et al., *J. Clin. Oncology* 14(4):1128-1135 (1996); Pitot, H. C., et al, *J. Clin. Oncology* 15(8):2910-2919 (1997); and Rothenberg, M. L., et al., *Cancer* 85(4):786-795 (1999).

The complete absence of severe (grade 3-4) gastrointestinal toxicity in the patients used in the study is striking, statistically highly significant, and clinically very important.

5.2. Example 2: Alternative Treatment of Colorectal Cancer

In this study, 5FU, leucovorin, irinotecan, and thalidomide are used in combination to treat metastatic colorectal cancer. Patients with histologically confirmed colon or rectal carcinoma are treated using six week cycles, which comprise the intravenous administration of 125 mg/m$^2$ of irinotecan over 90 minutes, followed by 20 mg/m$^2$ bolus administration of leucovorin, followed by 500 mg/m$^2$ bolus administration of 5FU. Each drug is administered weekly×4, followed by two weeks of rest. Thalidomide is administered daily and orally at a dose of 400 mg at bedtime. The response of each patient is assessed at the conclusion of each cycle using methods and criteria described herein and known to those skilled in the art.

5.3. Example 3: Treatment of Myelodysplastic Syndromes

The efficacy of using a combination of topotecan and thalidomide in improving the ineffective hematopoiesis of poor prognosis patients with myelodysplastic syndromes (MDS), patients with refractory anemia with excess blasts (RAEB) who have greater than about 15 percent blasts in the bone marrow (BM), RAEB in transformation (RAEB-t), and patients with chronic myelomonocytic leukemia (CMMoL) are determined as set forth below.

The treatment comprises administering topotecan hydrochloride (Hycamtin) by intravenous infusion (1.25 mg/M$^2$ over 30 minutes) to patients (RAEB>5%) for five days every 21 days, for three cycles (each cycle is 21 days). At the conclusion of the cycles, each patient is evaluated. If the blasts have decreased to less than about five percent or have decreased by half, the administration of thalidomide is begun: it is first administered orally at about 100 mg/day, and increased up to about 300 mg as tolerated for a maximum of about one year.

If, following the three initial cycles of topotecan therapy, the blasts are still greater than five percent, two additional cycles of topotecan are administered, after which thalidomide therapy is begun. As above, thalidomide is first administered orally at about 100 mg/day, and increased up to about 300 mg as tolerated for a maximum of about one year.

Frequent monitoring of peripheral blood cell counts are instituted during the treatment, since Hycamtin should only be administered to patients with adequate bone marrow reserves, including baseline neutrophil counts of at least 1,500 cells/mm$^3$ and platelet count of at least 100,000/mm$^3$. Other precautions taken during the study are well known to those skilled in the art.

During the therapy, apoptosis studies are performed on all bone marrow samples using flow cytometry (TUNNEL technique) or DNA laddering (gel electrophoresis or pulsed field electrophoresis) techniques. Proliferation studies are also performed to determine detailed cell cycle kinetics. Cytokine expression studies are also performed. In particular, TNF-α is measured by standard ELISA techniques on a weekly basis, while bone marrow aspirate is studied by sorting and measuring mRNA levels using multiplex RT-PCR for a variety of cytokines including IL1β, TNF-α, IL6, flt3 ligand, hSCF, and GM-CSF. An immunohistochemical detection of TNF-α and IL1-β is also performed on all biopsies.

5.4. Example 4: Treatment of Prostate Cancer

The efficacy of using a combination of docetaxel and thalidomide in the treatment of prostate cancer is determined as described below in patients with histologically confirmed prostate or pancreatic cancer. The efficacy of the combination is also determined with regard to progressive disease after therapy with gemcitabine in patients with pancreatic cancer or after androgen suppression therapy in patients with metastatic prostate cancer.

Patients who meet criteria known to those skilled in the art (e.g., those who are not pregnant, HIV-positive, or those with active brain metastasis) are intravenously administered docetaxel once weekly (Day 1) for a total of 24 weeks at a dose of 33 mg/m$^2$. Premedication with dexamethasone 8 mg PO Q6H×3 doses, starting 12 hours before the administration of docetaxel is given to decrease or prevent acute anaphylactoid reactions and to decrease the severity or delay the onset of late-occurring fluid retention problems.

Three days prior to starting treatment with thalidomide (Day 5), subjects are initiated on a bowel regimen to minimize the occurrence of constipation. On week 2 (Day 8), patients first receive thalidomide, which is administered daily at bedtime in four schedules using a weekly dose-escalation design. See, e.g., Gruber, M. L., et al., *Cancer Investigation* 2000;18 (suppl. 1):41 (abstract); Eisen T., *Cancer Investigation* 2000; 18 (suppl. 1):42 (abstract); and Figg. W., et al., *Cancer Investigation* 2000; 18 (suppl. 1):81 (abstract). Three patients are treated on the initial schedule. If no dose-limiting toxicities are observed, three patients are treated on the next schedule. If one of three patients treated on a schedule develops a dose-limiting toxicity, three additional patients are treated on that schedule. If two patients treated on a schedule develop dose-limiting toxicity, the maximum tolerated dose of thalidomide has been reached, and is defined to be the previous schedule (or to be a does below the initial dose if two patients develop dose-limiting toxicity on the first schedule). If only three patients have been treated on the previous schedule, then three additional patients are treated on the current one. If, at any time, the data suggest a significant hazard to further dose escalation, dose escalation is halted pending a review of the data.

Thalidomide is given daily until progression, unacceptable toxicity develops, or when the subject wishes to discontinue treatment. For subjects who are stable and show no signs of unacceptable toxicity, the maximum daily dose of thalidomide that is given in this regime is 200 mg, 400 mg, 600 mg, or 800 mg for each level shown in Table 2:

TABLE 2

Dose of Thalidomide (mg/day) as a Function of Week and Schedule

| WK | 1 | 2 | 3 | 4 | 5 | 6 | 7 | 8 |
|---|---|---|---|---|---|---|---|---|
| I | 50 | 100 | 150 | 200 | 200 | 2000 | 200 | 200 |
| II | 50 | 100 | 150 | 200 | 250 | 300 | 350 | 400 |
| III | 50 | 100 | 150 | 200 | 250 | 300 | 350 | 400 |
| IV | 50 | 100 | 150 | 200 | 250 | 300 | 350 | 400 |

| WK | 9 | 10 | 11 | 12 | 13 | 14 | 15 | 16 |
|---|---|---|---|---|---|---|---|---|
| I | 200 | 200 | 200 | 200 | 200 | 200 | 200 | 200 |
| II | 400 | 400 | 400 | 400 | 400 | 400 | 400 | 400 |
| III | 450 | 500 | 550 | 600 | 600 | 600 | 600 | 600 |
| IV | 450 | 500 | 550 | 600 | 650 | 700 | 750 | 800 |

Baseline radiographic studies are done for initial tumor measurements. Chest X-ray is done to measure pulmonary metastases, and a CT scan of the abdomen is done for those patients with liver or other abdominal metastases that are measurable using that modality. Baseline laboratory studies are also performed, such as serum biochemistry, hematological, PSA (prostate patients only), CA 19-9 (pancreatic patients only), pregnancy, and binding protein studies, as known to those skilled in the art. These studies are continued during treatment to determine its effectiveness, and to ensure the safety of each patient.

The embodiments of the invention described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method of treating primary cancer which comprises administering to a patient in need of such treatment a therapeutically effective amount of topotecan, or a pharmaceutically acceptable prodrug, salt, solvate, hydrate, or clathrate thereof, and a therapeutically effective amount of thalidomide, or a pharmaceutically acceptable prodrug, salt, solvate, hydrate, or clathrate thereof.

2. A method of treating metastatic cancer which comprises administering to a patient in need of such treatment a therapeutically effective amount of a topotecan, or a pharmaceutically acceptable prodrug, salt, solvate, hydrate, or clathrate thereof, and a therapeutically effective amount of thalidomide, or a pharmaceutically acceptable prodrug, salt, solvate, hydrate, or clathrate thereof.

3. The method of claim 1 or 2 wherein the cancer is cancer of the head, neck, eye, mouth, throat, esophagus, chest, bone, lung, colon, rectum, stomach, prostate, breast, ovaries, kidney, liver, pancreas, and brain.

4. The method of claim 3 wherein the cancer is colon or rectal cancer.

5. The method of claim 1 or 2, wherein the thalidomide, or pharmaceutically acceptable prodrug, salt, solvate, hydrate, or clathrate thereof, is administered in an amount of from about 1 to about 2000 mg.

6. The method of claim 5 wherein the thalidomide, or pharmaceutically acceptable prodrug, salt, solvate, hydrate, or clathrate thereof, is administered in an amount of from about 50 to about 1000 mg.

7. The method of claim 6 wherein the thalidomide, or pharmaceutically acceptable prodrug, salt, solvate, hydrate, or clathrate thereof, is administered in an amount of from about 100 to about 750 mg.

8. The method of claim 7 wherein the thalidomide, or pharmaceutically acceptable prodrug, salt, solvate, hydrate, or clathrate thereof, is administered in an amount of from about 200 to about 500 mg.

9. The method of claim 1 or 2, wherein thalidomide is administered.

10. The method of claim 1 or 2, wherein the thalidomide salt or solvate is administered.

* * * * *